United States Patent
Frigo et al.

(10) Patent No.: US 12,121,748 B2
(45) Date of Patent: Oct. 22, 2024

(54) SYSTEM AND METHOD FOR ASSESSING RADIATION THERAPY PLAN CALCULATION ACCURACY

(71) Applicant: WISCONSIN ALUMNI RESEARCH FOUNDATION, Madison, WI (US)

(72) Inventors: Sean Frigo, Madison, WI (US); Wesley Culberson, Madison, WI (US); John Stasko, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 182 days.

(21) Appl. No.: 17/830,162

(22) Filed: Jun. 1, 2022

(65) Prior Publication Data
US 2023/0390581 A1    Dec. 7, 2023

(51) Int. Cl.
*A61N 5/10*    (2006.01)

(52) U.S. Cl.
CPC ......... *A61N 5/1036* (2013.01); *A61N 5/1038* (2013.01); *A61N 5/1045* (2013.01); *A61N 2005/1041* (2013.01)

(58) Field of Classification Search
None
See application file for complete search history.

(56) References Cited

U.S. PATENT DOCUMENTS

| | | | |
|---|---|---|---|
| 2003/0086530 A1* | 5/2003 | Otto | A61N 5/1042 378/65 |
| 2015/0314139 A1* | 11/2015 | Burt | A61N 5/1067 600/1 |
| 2019/0143147 A1* | 5/2019 | Isola | A61N 5/103 378/65 |

OTHER PUBLICATIONS

Chang KH et al., "Clinical Implications of High Definition Multileaf Collimator (HDMLC) Dosimetric Leaf Gap (DLG) Variations," Prog Med Phys. 2016;27(3): 111. doi:10.14316/pmp.2016.27.3.111.
Chen Y et al., "Calculation of x-ray transmission through a multileaf collimator," Med Phys. 2000;27(8): 1717-1726. doi: https://doi.org/10.1118/1.1286555.
Chiavassa et al., Complexity metrics for IMRT and VMAT plans: A review of current literature and applications. Br J Radiol. 2019; 92(1102). doi:10.1259/bjr.20190270.
Granville D.A. et al., "Predicting VMAT patient-specific QA results using a support vector classifier trained on treatment plan characteristics and linac QC metrics," Phys. Med. Biol., vol. 64, No. 9, 2019.

(Continued)

*Primary Examiner* — Hoon K Song
(74) *Attorney, Agent, or Firm* — Quarles & Brady, LLP

(57) ABSTRACT

A system and method are provided for assessing a radiation therapy plan to be implemented on a particular radiation therapy system that includes a multi-leaf collimator (MLC). The method includes receiving a radiation therapy plan and calculating at least one metric indicating transmission characteristics of a beam delivered using the particular radiation therapy system to perform the radiation therapy plan using a model of the MLC having a plurality of zones, wherein each zone is classified based on the transmission characteristics. The method also includes evaluating the at least one metric against a tolerance for variation between the radiation therapy plan and an implementation of the radiation therapy plan on the particular radiation therapy system and generating an alert indicating that the at least one metric is outside the tolerance.

17 Claims, 7 Drawing Sheets

(56) References Cited

OTHER PUBLICATIONS

Interian Y. et al., "Deep nets vs expert designed features in medical physics: An IMRT QA case study," Med. Phys., vol. 45, No. 6, pp. 2672-2680, 2018.
Kumaraswamy et al., "Spatial Variation of Dosimetric Leaf Gap and the Impact in Dose Delivery," Med. Phys. 41 (11), Nov. 2014.
Lam D. et al., "Predicting gamma passing rates for portal dosimetry-based IMRT QA using machine learning," Med. Phys., vol. 46, No. 10, pp. 4666-4675, 2019.
Nyflot M.J. et al., "Deep learning for patient-specific quality assurance: Identifying errors in radiotherapy delivery by radiomic analysis of gamma images with convolutional neural networks," Med. Phys., vol. 46, No. 2, pp. 456-464, 2019.
Rangel et al., "Tolerances on MLC leaf position accuracy for IMRT delivery with a dynamic MLC," Med. Phys., (2009) 36(7):3304-3309. doi:10.1118/1.3134244.
Tomori S. et al., "A deep learning-based prediction model for gamma evaluation in patient-specific quality assurance," Med. Phys., vol. 45, No. 9, pp. 4055-4065, 2018.
Valdes G. et al., "A mathematical framework for virtual IMRT QA using machine learning," Med. Phys., vol. 43, No. 7, pp. 4323-4334, 2016.
Valdes G. et al., "IMRT QA using machine learning: A multi-institutional validation," J. Appl. Clin. Med. Phys., vol. 18, No. 5, pp. 279-284, 2017.
Wall et al., "Application and comparison of machine learning models for predicting quality assurance outcomes in radiation therapy treatment planning," Informatics Med. Unlocked, vol. 18, p. 100292, 2020.

\* cited by examiner

SYSTEM AND METHOD FOR ASSESSING RADIATION THERAPY PLAN CALCULATION ACCURACY

STATEMENT REGARDING FEDERALLY SPONSORED RESEARCH

N/A

BACKGROUND

The present disclosure relates to systems and methods for radiation therapy. More particularly, systems and methods are provided for performing quality assurance for radiation therapy plans, for example, when employing a multi-leaf collimator.

Radiation therapy (RT) has gone through a series of technological revolutions in the last few decades. With intensity modulated RT (IMRT), it became possible to produce highly conformal dose distributions, whereby the bulk radiation dose is delivered to the extent of a tumor target. One key component of an IMRT system and other sophisticated RT systems is a multi-leaf collimator (MLC). On a linear accelerator-based treatment delivery system, an MLC is generally formed of a plurality of tungsten or other radio-opaque panels or "leaves" that can be manipulated to adjust the shape of the radiation beam that is delivered to the patient. The particular shape of the MLC formed by the specific positions of the leaves at any given time is dictated by a radiation therapy plan that is carefully designed before the radiation therapy procedure. A single static set of leaf positions is collectively referred to as a shape or control point. A plan consists of a sequence of control points.

The radiation therapy plan seeks to specify all aspects of the radiation therapy delivery, including the use of the MLC and/or the specifics of intensity modulation, against many other variables and controls, such as patient position, source position, and so on. Thus, a radiation therapy plan is carefully designed to produce a complex set of control parameter values in order to achieve a particular therapeutic effect, which is generally to deliver a desired dose of radiation to a tumor, while minimizing the dose of radiation delivered to surrounding healthy tissue.

To calculate the dose delivered by a radiation therapy plan, a variety of "models" of the real-world systems are utilized. For example, the radiation beam source is one model. The MLC and its ability to modulate the intensity is another model. The patient, the tumor, and position of healthy tissue relative to the location and boundaries of the tumor are represented by other models.

Unfortunately, these models can differ from the real-world systems that they represent. As a result, despite extensive effort building a radiation therapy plan using the models, it is a general clinical practice to perform an extensive quality assurance process using dose measurement tools before delivering the radiation therapy plan to the patient. That is, despite all the planning and modeling, it is a general clinical practice to utilize test objects called phantoms, and other testing/calibration tools, to ensure that the plan is realized as designed once it is implemented in the real world. This testing and quality assurance process is labor/personnel-intensive, but undertaken because there is non-zero risk that the models for building the plan and the real-world implementation of the plan can differ substantially.

Therefore, it would be desirable to have systems and methods to help ensure that radiation therapy models and the real-world implementation of the related plans are sufficiently consistent to ensure proper patient results without relying on extensive manual quality assurance testing executed as dry runs.

SUMMARY

The present disclosure overcomes the aforementioned drawbacks by providing systems and methods for assessing or verifying radiation therapy plans for delivery using a given real-world therapy system without relying on phantoms or quality assurance dry-run verification processes. In particular, systems and methods are provided that are able to predict real-world results and, assess whether the results are sufficiently correlated to the desired results underlying the radiation therapy plan, in order to approve the use of the plan with a patient without the need for quality assurance measurements. For example, systems and methods are provided to automatically analyze a candidate treatment plan's delivery instruction control point data. The system and method can identify if a plan would produce a measurement outcome outside of acceptable ranges, and flag for review and adjustment before use in the real world. In particular, systems and methods are provided for assessing a given radiation-therapy plan relative to a given radiation-therapy system including an MLC.

In accordance with one aspect of the present disclosure, a system is provided for assessing a radiation therapy plan includes a radiation therapy system configured to deliver radiation therapy to subject based on a radiation therapy plan and including a multi-leaf collimator (MLC). The system also includes a computer system configured to receive the radiation therapy plan and calculate at least one metric indicating transmission characteristics of a beam delivered according to the radiation therapy plan using a model of the MLC having a plurality of zones, wherein each zone is classified based on transmission characteristics. The computer system is further configured to assess the at least one metric against a tolerance for variation between the radiation therapy plan and an implementation of the radiation therapy plan on the radiation therapy system and generate an alert if the at least one metric is outside the tolerance.

In accordance with another aspect of the present disclosure, a method is provided for assessing a radiation therapy plan to be implemented on a particular radiation therapy system that includes a multi-leaf collimator (MLC). The method includes receiving a radiation therapy plan and calculating at least one metric indicating transmission characteristics of a beam delivered using the particular radiation therapy system to perform the radiation therapy plan using a model of the MLC having a plurality of zones, wherein each zone is classified based on the transmission characteristics. The method also includes evaluating the at least one metric against a tolerance for variation between the radiation therapy plan and an implementation of the radiation therapy plan on the particular radiation therapy system and generating an alert indicating that the at least one metric is outside the tolerance.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION

Figure 1:
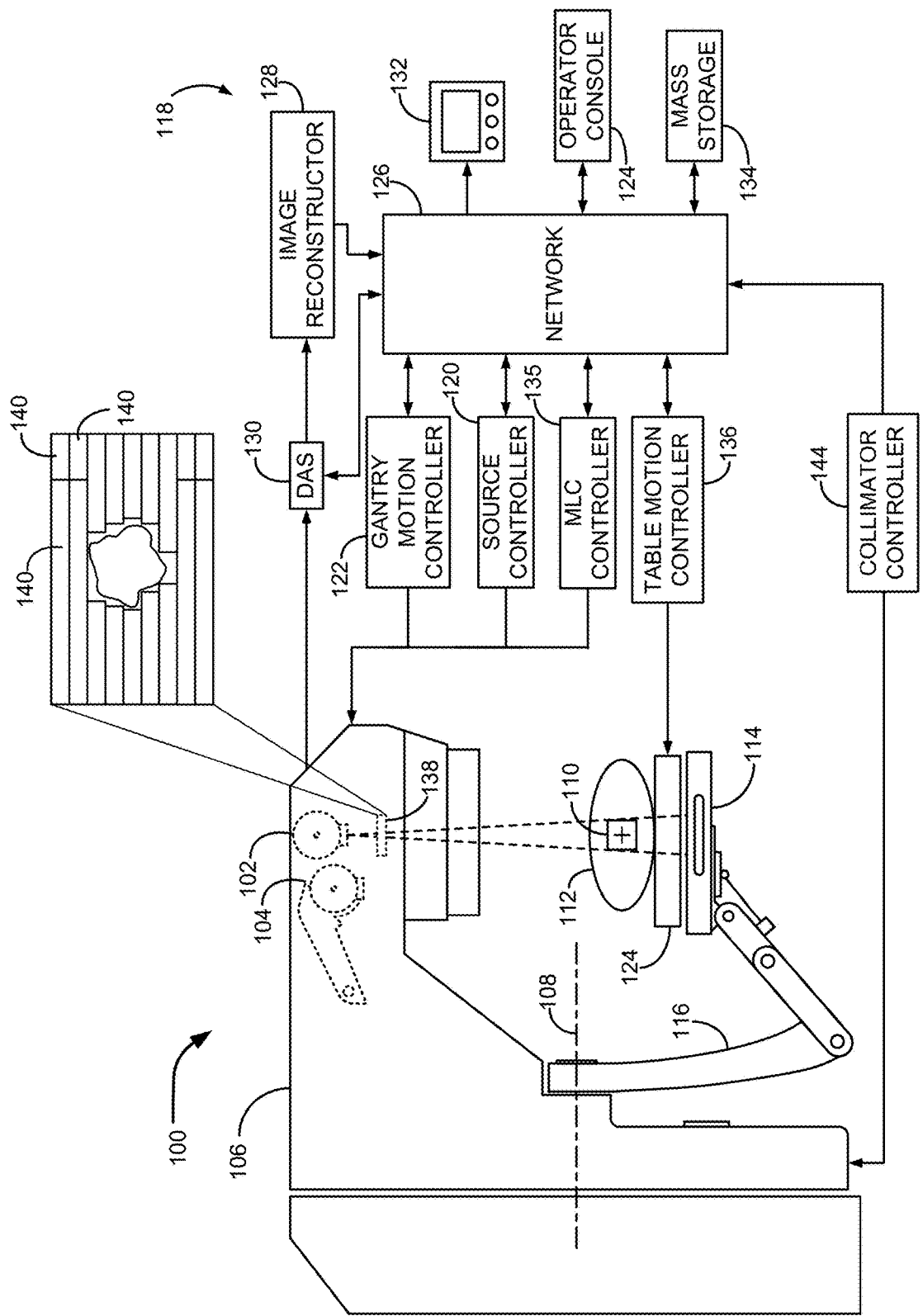
FIG. 1 is a schematic diagram of an example system in accordance with the present disclosure and that can be configured to implement the methods described herein.

Referring to FIG. 1, an example of a c-arm radiation therapy system 100. The radiation therapy system 100 includes a therapeutic radiation source 102 and an on-board imaging source 104. As will be described, the systems and methods of the present disclosure can use the on-board imaging system to as part of a quality assurance measurement system to establish the reference dataset. The radiation source 102 and the on-board imaging source 104 may be housed in the same gantry system 106 or may be mounted orthogonally to the radiation source 102. The radiation therapy system 100 may include any suitable radiation treatment system, including image-guided radiation therapy ("IGRT") systems, intensity-modulated radiation therapy ("IMRT") systems such as intensity-modulated arc therapy ("IMAT") and volumetric modulated arc therapy ("VMAT") systems, an external beam radiotherapy delivery system, such as a linear accelerator ("LINAC"), proton radiotherapy systems, helical photon radiotherapy systems (Tomotherapy), non-isocentric photon radiotherapy systems (Cyberknife®), and isotope based radiotherapy systems (ViewRay™ and GammaKnife®), and the like. In a non-limiting example, the radiation therapy system is a Truebeam™ c-arm linear accelerator with 6MV photons and standard definition (SD) multileaf collimator (MLC). The treatment beam for the radiation therapy system can be composed of photons, neutrons, electrons, protons, heavy charged particles, or the like. Specific treatment plans can also be designed and delivered in order to evaluate key parameters of each radiotherapy system. Clinically relevant treatment plans, prepared in an ancillary treatment planning system, are utilized with the system 100. As will be described, the system 100 may be configured to implement systems and methods of the present disclosure, and/or other, separate systems, including computer systems, may be configured to implement the systems and methods of the present disclosure.

The on-board imaging source 103 may be included in the system 100 and, if so, may include an x-ray source as part of a cone-beam computed tomography ("CBCT") system, a computed tomography ("CT") system, and the like. Alternatively, the imaging may be performed by a separate diagnostic fan-beam x-ray or magnetic resonance imaging system. In the illustrated configuration, both the therapeutic radiation source 102 and imaging source 104 are attached adjacent each other and housed at the same end of a rotatable gantry 106, which rotates about a pivot axis 108. The rotatable gantry 106 allows either of the sources, 102 and 104, to be directed in a desired manner with respect to a target volume 110 in a subject 112 positioned on a table 114 supported by a table support 116.

The rotation of the rotatable gantry 106, the position of table 114, and the operation of the sources, 102 and 104, are governed by a control system 118 of the radiation therapy system 100. The control system 118 includes a source controller 120 that provides power and timing signals to the radiation source 102 and imaging source 104, and receives image data therefrom. A gantry motion controller 122 controls the rotational speed and position of the gantry 106. The control system 118 communicates with an operator console 124 and other parts of a network 126 through a communication system. An image reconstructor 128, receives sampled and digitized image data over the network 126 or from the data acquisition system 130 and performs image reconstruction.

Plan data can be received from a treatment management system database over a network. Commands and delivery parameter values can be communicated to the treatment delivery system via the operator console 124. The operator console 124 may include a variety of user interfaces, including a display 132 and may have access to mass storage 134. The operator-supplied commands and parameters are used by the computer 109 to provide control signals and information to an imaging controller, and communicate with the source controller 120, the gantry motion controller 122, the MLC motion controller 135 and a table motion controller 136 to effectuate a radiation therapy delivery process in accordance with a radiation therapy plan.

Still referring now to FIG. 1, the radiation source 102 produces a divergent radiation beam, or "field," which in some forms may be conical or any other shape, emanating from a focal spot and directed toward the subject 112. In a traditional radiation therapy system, the radiation beam is collimated by a collimator 138 that is mounted proximal to and designed to move with rotation of the radiation source 102 about the axis 108. The collimator 138 is secured in the gantry 106 in a fixed position relative to the radiation source 102. The collimator 138 may be a multi-leaf collimator (MLC), for example, constructed of a set of movable rectangular blades, which may include features such as rounded ends to, form a generally planar conical radiation beam centered about radiation beam's central axis. Each leaf 140 of the collimator 138 is constructed of a dense radio-opaque material such as lead, tungsten, cerium, tantalum, or related alloy.

To create a radiation therapy plan for the system 100, software is used that models how the system 100 will perform given various selected operational choices, such as the position of the source 102 relative to the subject 112, intensity of the source 102 at a position, and adjustment of the collimator 138 at each position. The delivery instructions are embodied within a set of data called a treatment plan. Once the therapy plan is created, it must be validated by performing a "dry run" of the system 100 performing the therapy plan with a phantom, instead of the subject 112. This "dry run" allows clinicians to identify if the models of the planning software were inaccurate or yielded incorrect outputs relative to the actual delivered therapeutic dose by hardware of the system 100. Of course, performing such a "dry run" is labor intensive and time consuming. It represents a substantial inefficiency in clinical care.

As will be described, the present disclosure provides systems and methods to analyze radiation therapy plans, such as may be implemented using the system 100, without needing to carry out the whole therapy plan using the system 100 and related measurement equipment. The systems and methods provided herein are capable of classifying the transmission array for each MLC shape, and compute several metrics based on the relative contributions of each classified sub-region. As will be described, the systems and methods provided herein are capable of performing quality assurance with a speed, efficiency, and accuracy that has never been realized. Even modest improvements in quality assurance or accuracy between the radiation therapy plan and the realization of the plan in the real world, such as delivery using the system 100, can greatly improve clinical outcomes. For example, a 0.6 mm change in dosimetric leaf gap (DLG) has been found to lead to 2% change in dose for sliding window head and neck IMRT plans, as described in Rangel A, Dunscombe P. Tolerances on MLC leaf position accuracy for IMRT delivery with a dynamic MLC. *Med Phys*. 2009; 36(7):3304-3309. Furthermore, improvements in QA efficiency frees up staff to focus on complicated individual tasks or more time on existing tasks. Both can improve overall quality and accuracy by virtue of having more time available. By providing consistent systems for assessing and assuring the quality or accuracy of the radiation therapy plan as realized in the real world, clinical procedures will improve, and clinical outcomes will correspondingly improve.

Figure 2:
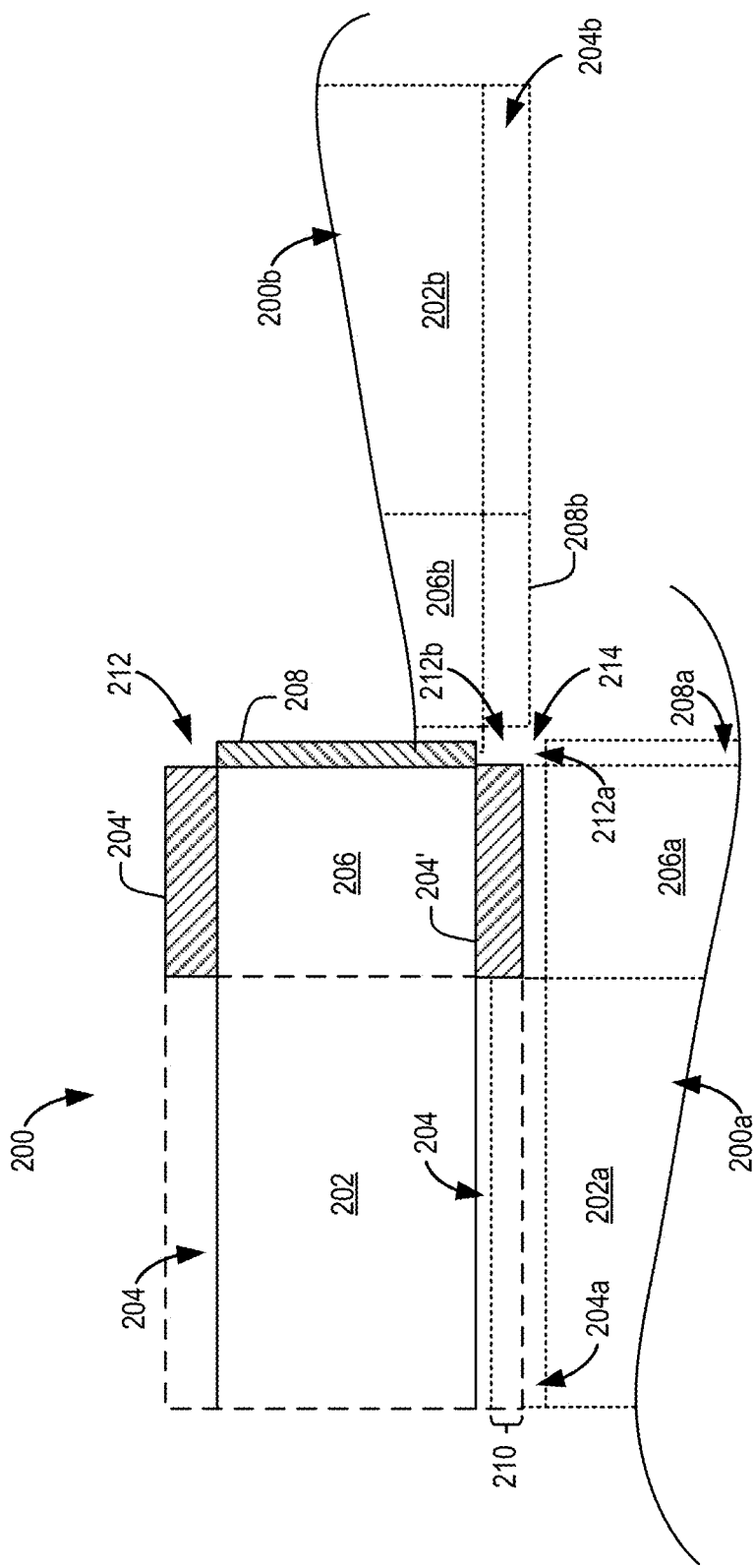
FIG. 2 is a schematic diagram of a model of a given leaf of a multi-leaf collimator having a plurality of zones or classifications, in accordance with the present disclosure.

By definition, all calculation models are representations of reality, typically, built upon assumptions and simplifications. For example, many treatment planning systems employ simplified MLC transmission functions. The present disclosure recognizes that MLC transmission functions not only vary based on the different regions of a leaf in the MLC, but that certain regions are more prone to error and/or increase the complexity of the plan. For example, referring to FIG. 2, a given leaf model 200 of an MLC may be formed of a plurality of "zones" 202, 204, 206, and 208. Though four zones 202, 204, 206, and 208 are illustrative, many more zones may be present for a given MLC design. Zone definition can include, but not be limited to, a specific treatment planning system MLC model or the physical dimensions of the employed MLC leaves in question.

Each of the zones 202-208 can have different transmission characteristics. For example, zones 202 and 206 are substantially uniform and have consistent transmission properties. On the other hand, zones 204 and 204' may have a "tongue-and-groove" or other profiles designed to accommodate interfacing with an adjacent leaf 200a, 200b. In this way, the transmission profile properties of zones 204 and 204' may differ substantially from zones 202, 206, and 208. Furthermore, zones 204, 204' and 208 may differ substantially from each other. Further still, zones 204 and 204' may have transmission profiles similar to zones 202 and 206 if/when engaged with an adjacent leaf 200a, 200b, such as when fitting together with the adjacent leaf 200a, 200b in a "tongue-and-groove" or similar complementary arrangement. However, as illustrated, the "tongue-and-groove" arrangement between zones 204 and 204a may not align perfectly, such that only an overlapping portion 210 has a transmission profile similar to zones 202, 202a, 202b, 206, 206a, or 206b. Thus, the transmission profile of zones 204 and 204a on either side of the overlapping portion 210 will be greater in the real world than a model that assumes that zones 204 and 204a overlap perfectly.

To add yet further complexity, the leaf model 200 may include void zones 212, where there is material and reduced transmission in a real-world MLC, but treated as open space by the treatment planning system MLC model. Thus, in accordance with the present disclosure, each zone may be assigned a classification. These void zones 212, 212a, 212b may compound to create a void area 214. The classification may describe the transmission profiles of the zone and/or potential characteristics of the interaction of the zones. Furthermore, the classification may describe the transmission profiles of the zone and/or potential characteristic in the face of maintenance needs or the potential for damage from use that could change the transmission profile. Some non-limiting examples include:

| Classification | Description |
| --- | --- |
| Open | Does not belong to leaf body, leaf tip, or tongue and groove regions of the MLC |
| Calibration | Belongs to open region only after applying the shift from the position calibration |
| Tip | Belongs to leaf tip region defined by the post-calibration leaf position, the leaf tip width, and the entire extent of the leaf in the direction perpendicular to the leaf's travel |
| Body | Belongs to leaf body region defined by end of the leaf tip, the jaw from which the MLC bank protrudes, and the perpendicular extent of the leaf minus the tongue and groove regions on both sides |
| Paired | Belongs to tongue and groove region where the neighboring regions perpendicular to the leaf's travel are either leaf body or leaf tip |
| Exposed | Belongs to tongue and groove region where the neighboring regions perpendicular to the leaf's travel are leaf body and open field |
| Neglected | Belongs to tongue and groove region where the neighboring regions perpendicular to the leaf's travel are leaf tip and open field |

Table 1. MLC transmission region classifications and their corresponding descriptions.

The systems and methods provided herein utilize zones and classifications of the zones, such as described above, and plan properties to assess the complexity or modeled consistency of a given plan to perform an assessment of a plan without requiring a "dry run" measurement of the plan. In this way, the present disclosure provides systems and methods that can assist clinicians with ensuring that the modeled dose to be delivered by the radiation therapy plan is within a desired tolerance.

Figure 3:
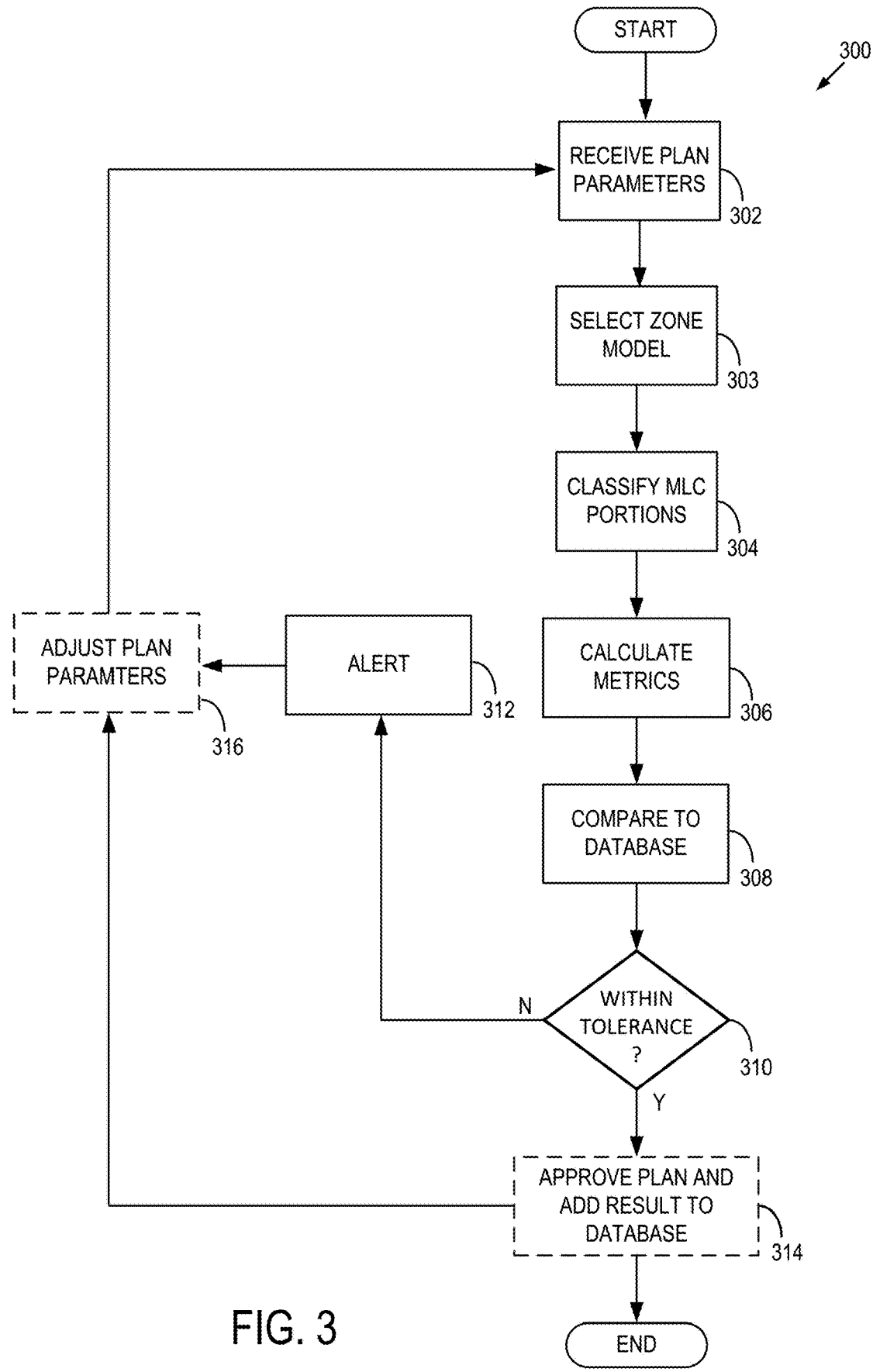
FIG. 3 is a flowchart setting forth some non-limiting example steps of a process in accordance with the present disclosure.

Specifically, referring to FIG. 3, a flowchart is provided that sets for some non-limiting steps of a process 300 in accordance with the present disclosure, such as may be implemented using part or more of the system 100 of FIG. 1, or other computers or systems with processors programmed as will be described.

At process block 302, the parameters for a radiation therapy plan that has been created are received. In one non-limiting example, these may include several inputs from the user and/or components of a radiation therapy plan and/or a complete radiation therapy plan. In one non-limiting example, a DICOM RT-Plan file may be received/input. In one further non-limiting example, the plan may have been generated using a RayStation treatment planning system, available from RaySearch Laboratories, Stockholm, Sweden. However, any other plan or plan generating system may also be used. Regardless of the plan and/or parameters received, the system may extract information such as MLC position and transmission, MLC model parameter values or other descriptions of MLC geometry, or other information. This information may be used to create or select a zone model, such as described with respect to FIG. 2, and/or to evaluate the plan parameters using the zone model.

At process block 303, zone models are selected that correspond to the radiation therapy system and/or the MLC of the radiation therapy system that will be utilized to implement the plan from which the parameters were received at process block 302. In accordance with one aspect of the disclosure, zones can be defined based on a treatment planning system-specific MLC model and a clinic's specific set of model parameter values. For example, some systems, such as RayStation, use a position calibration to shift the position of the MLC leaf tips. This calibration is a quadratic function of the leaf's DICOM position. Thus, the three coefficients of the function (offset, gain, and curvature) can be extracted from an existing clinically utilized beam model. Other parameter values, such as tip width and tongue and groove width can also be used.

At process block 304, the received parameters are used to classify each MLC or MLC portion throughout the plan, using the zones and corresponding classifications, such as described above. For example, with this information, a first control point of the first beam in the plan can be evaluated for each leaf in the MLC. As described above, using the zones and classifications, each leaf in the MLC may be treated as a two-dimensional plane of rectangular zones with particular transmission characteristics described by the classification of each zone. The extent of this plane can be defined by the X and Y jaws in order to expedite calculation but can also span the entire range of mechanically available MLC positions. Either way, points in this plane can be sampled on a grid using a desired spacing in both dimensions. For example, this spacing may be 0.1 mm. Each point can be assigned a classification based on the zone that it belongs to. In one non-limiting example, the seven classifications provided in Table 1 can be utilized. Additionally, instead of using a fixed grid array to track zone location and extent, one may use explicit analytic geometric boundaries using lines and rectangles to demarcate the zones comprising a given control point. In this latter implementation, the areas of the zones can be determined and collected for later analysis.

With all classifications complete, metrics are calculated at process block 306. For each control point, the fraction of the total number of points in the grid belonging to each classification can be calculated. If zones are defined analytically, the area of each zone can be stored instead of point values. These "grid point fractions" can be recorded, and then the next control point can be calculated, and so on. This process can be repeated for every control point of every beam of the plan. Additionally, or alternatively, using the computed grid point fractions, an average value for each classification type can be calculated. This may be achieved using any of a variety of constructs. For example, averaging the grid point fractions can be done by an arithmetic average or a monitor unit (MU)-weighted average, or other method. Additionally, these averages can be calculated for each beam or the entire plan.

In one non-limiting example, the MU-weighted average grid point fractions for the entire plan can be used for comparison with known measured QA metrics for a set of representative plans. The average over the entire plan is most representative of the entire treatment. Also, weighting by the monitor units delivered at each control point adjusts for the importance of each control point on the resulting dose distribution. Control points with a small number of monitor units are less influential, while control points with more monitor units may more greatly affect the delivered dose. With this in mind, the averages can be calculated as:

$$\text{Plan } MU\text{-Weighted Average} = \frac{\sum_{i=1}^{N} f_i * m_i}{\sum_{i=1}^{N} m_i}. \quad [1];$$

where $f_i$ is the grid point fraction for the i-th control point, $m_i$ is the monitor units for the i-th control point, and N is the total number of control points in the plan. This average can be computed for all classification types, such as the above-listed, non-limiting list of seven classifications provided in Table 1.

Additionally, the grid point fraction for each control point can be normalized. In one, non-limiting example, this can be done using the open field fraction. Doing so can help differentiate plans that have similar average grid point fractions, but significantly different open field areas. For example, this might occur when comparing a VMAT plan and a 3DCRT plan that happen to have similar jaw positions. The equation for the normalized averages is as follows:

$$\text{Normalized Plan } MU\text{-Weighted Average} = \frac{\sum_{i=1}^{N} \frac{f_i}{o_i} * m_i}{\sum_{i=1}^{N} m_i}. \quad [2].$$

In the normalized version, the change relative to equation [1] is dividing the grid point fraction by the open field grid point fraction, $o_i$, at each control point.

Either or both of these metrics can then be compared to a database at process block 308. The database can store metrics and measurement results for a variety of known reference plans. Using the database, the metrics calculated at process block 306 are compared to known, similar plans with parameters similar to those provided at process block 302 with known metrics. In one non-limiting example, the metrics represent a comparison of ray tracing through modeled zones of the MLC indicated by the plan parameters provided at process block 302 against known ray tracing through actual MLCs, as stored in the database. Thus, the metrics provide useful information about the analyzed plan, by revealing what fraction of the beam passes through each part of the MLC leaves. If any of the grid point fractions and/or average grid point fractions and/or normalized grid point fractions do not correlate with plan evaluation metrics stored in the database, then the plan may be flagged or rejected, as will be described.

In particular, at decision block 310, the comparison of the metrics against the database yields an error that is evaluated against a tolerance. The tolerance may be assessed based on grid point fractions and/or average grid point fractions and/or normalized grid point fractions. Additionally, or alternatively, further metrics may be assessed, such as a percentage of the plan with the beam passing through particular zones or zone with particular classifications. In the later case, a "fingerprint" of the plan may be created that represents, in essence, a risk profile or potential for error given the reliance on particular zones/classifications by a given plan. In this way, at decision block 310, the tolerance may consider such a fingerprint in addition to or alternatively to assessing the above metrics directly.

The tolerance may be learned or may be predetermined. In either case, if not within the tolerance, an alert is generated at process block 312, which can be used to trigger an adjustment to the plan parameters at optional process block 316 and the process restarts at process block 312 as the new parameters are received. However, if within tolerance at decision block 310, the plan is approved and the results, such as metrics and/or parameters, can, optionally, be added to the database at process block 314. In this way, the database may be part of a machine learning or artificial intelligence system to have the tolerance evaluated at decision block 310 be adaptive, or it may simply add a value to a static dataset.

Regardless of whether the plan and results are stored into the database at process block 314, the process 300 may be configured for real-time adaptation and evaluation. That is, beyond using the process 300 to evaluate a plan before implementation with the subject/patient, the process 300 can also, optionally or alternatively, be used to evaluate plans in real time. That is the process 300 can be used to facilitate adaptations to the plan, even during execution of the plan to ensure that the adaptation will be safe and effective, and/or be more effective than the plan before the adaptation. Thus, the process 300, can include a loop for receiving adjusted plan parameters at process block 316 that causes the process to iterate 300. Such changes can be made on the day of therapy, or even during therapy, which is impractical when using traditional quality assurance procedures.

Example

The above-described process was used to evaluate actual plans against real-world systems. In one, non-limiting example, the grid point fractions and their corresponding averages were verified using a test plan, which consisted of several beams. The first beam was a 30×30 cm² square field, as defined by the jaws, with completely closed MLC leaves along the center of the field, except for one MLC leaf retracted by 0.5 cm, creating a 0.5×0.5 cm² field. The following beams consisted of static square fields between 1×1 cm² and 28×28 cm². From these simple geometries, each grid point fraction could be calculated manually by knowing the dimensions of the leaf tip, leaf body, and tongue and groove regions. The hand-calculated grid point fractions were compared to the computed fractions. In all cases, the values were nearly identical, with the largest differences being on the order of one in one million, significantly below the order of clinical significance. Any observed differences were the result of floating point precision errors.

The three-dimensional dose distribution for each plan was measured using a Delta4 Phantom+ system (Scandidos, Uppsala, Sweden). The gamma analysis pass rate (2% local dose difference criterion, 2 mm distance-to-agreement criterion, 10% threshold) and median dose deviation ((measured-calculated)/measured*100, 50% threshold) for each plan was calculated. Also, the average grid point fractions were compared to the gamma passing percentage and median dose deviation values to determine if a relationship between them existed. All measurement results were corrected for machine output variations.

Figure 4:
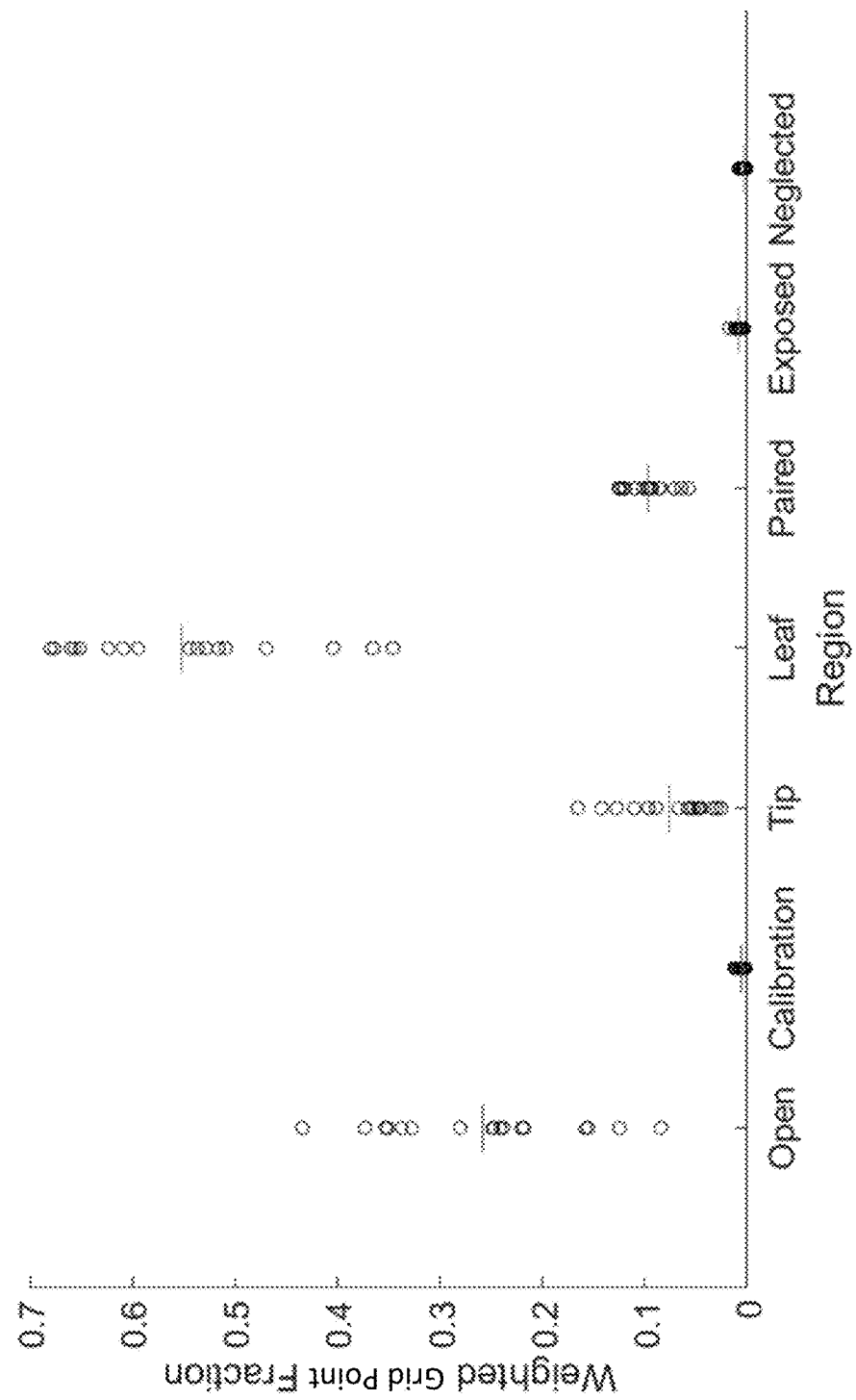
FIG. 4 is a plot of plan MU-weighted average grid point fractions for all plans, in accordance with the present disclosure.

FIG. 4 shows average grid point fractions for all plans that were evaluated. The open, tip, body, and paired tongue and groove grid point fractions all show a large range of values, indicating that the metrics may be useful in differentiating the plans. However, the calibration, exposed tongue and groove, and neglected tongue and groove grid point fractions were all clustered in a small range of values. This was expected, as those regions are small in all plans. FIG. 4 demonstrates the ability to differentiate plans based on the proposed metrics where the spread in values show broad ranges.

Figure 5A:
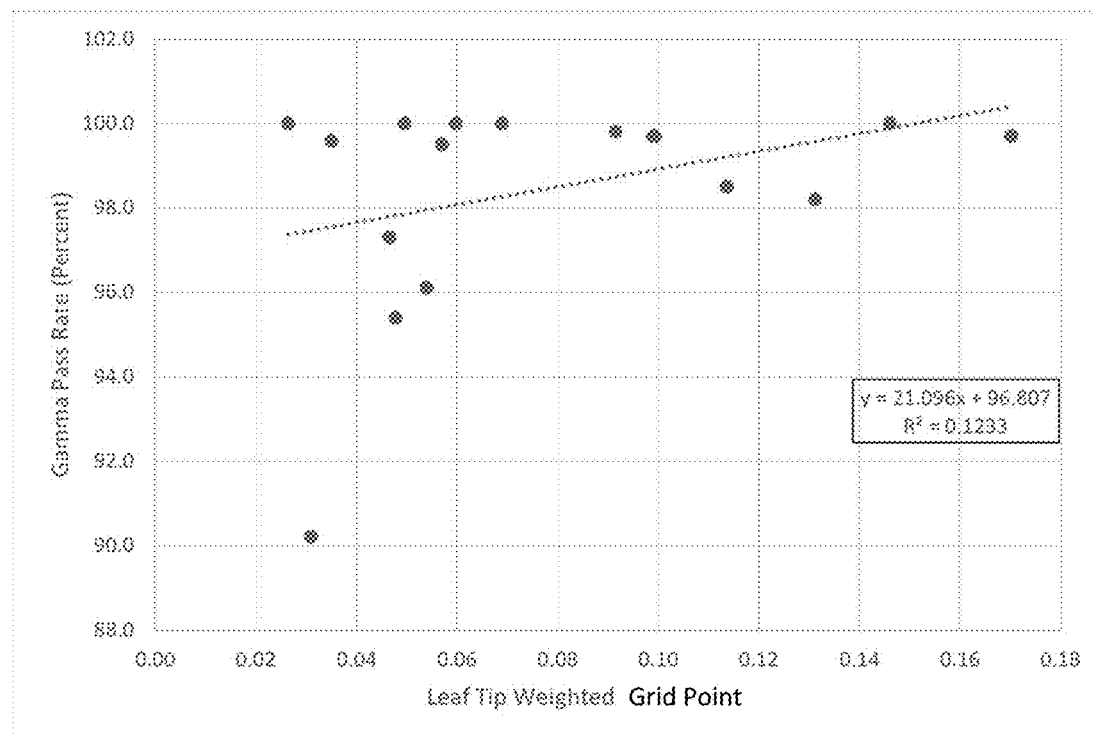
FIG. 5A is a graph of gamma analysis pass rates vs. plan MU-weighted average leaf tip grid point fractions, in accordance with the present disclosure.
Figure 5B:
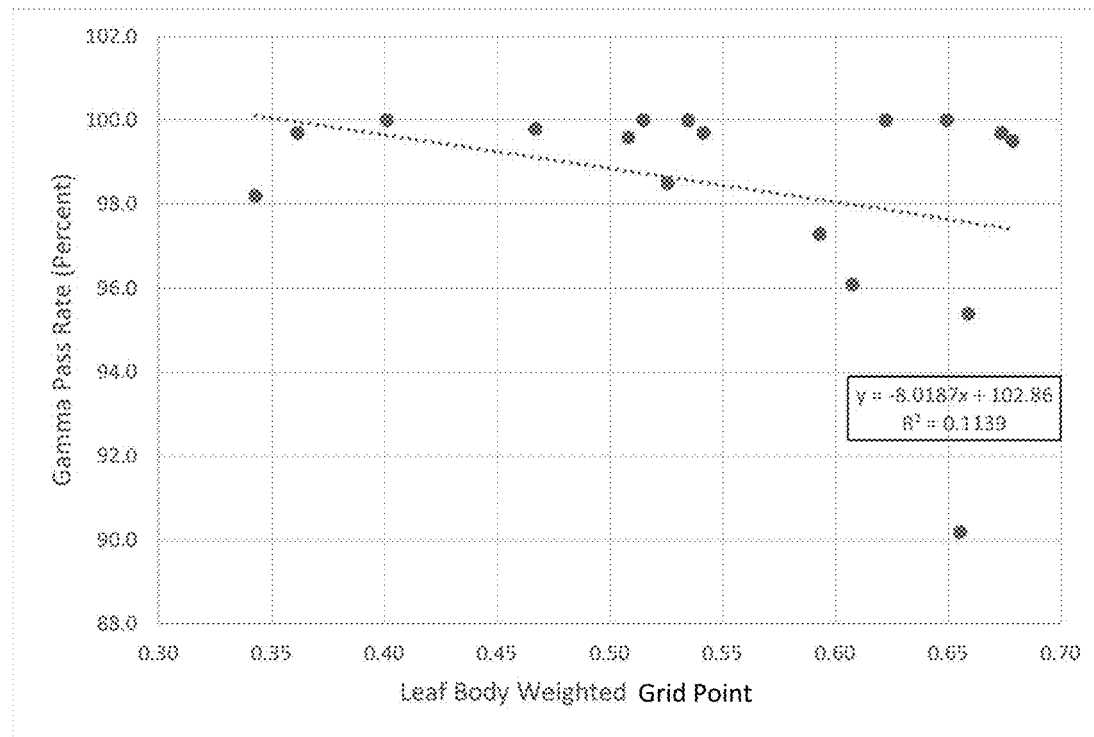
FIG. 5B is a graph of gamma analysis pass rates vs. plan MU-weighted average leaf body grid point fractions, in accordance with the present disclosure.
Figure 6A:
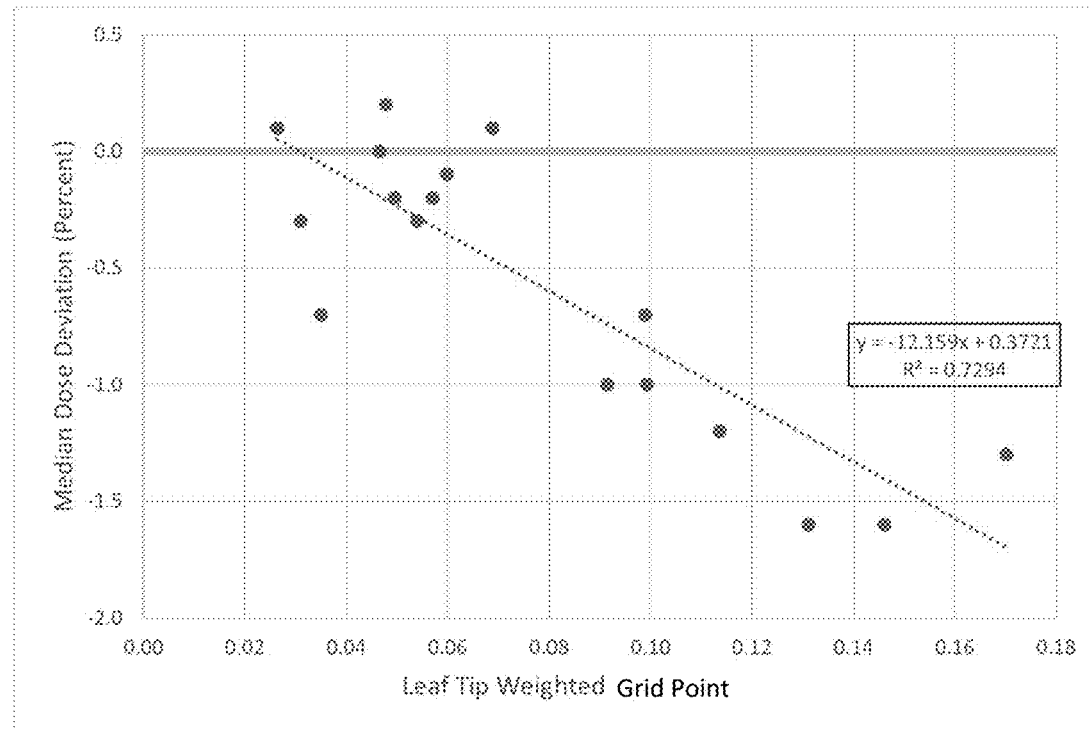
FIG. 6A is a graph of median dose deviation vs. plan MU-weighted average leaf tip grid point fractions, in accordance with the present disclosure.
Figure 6B:
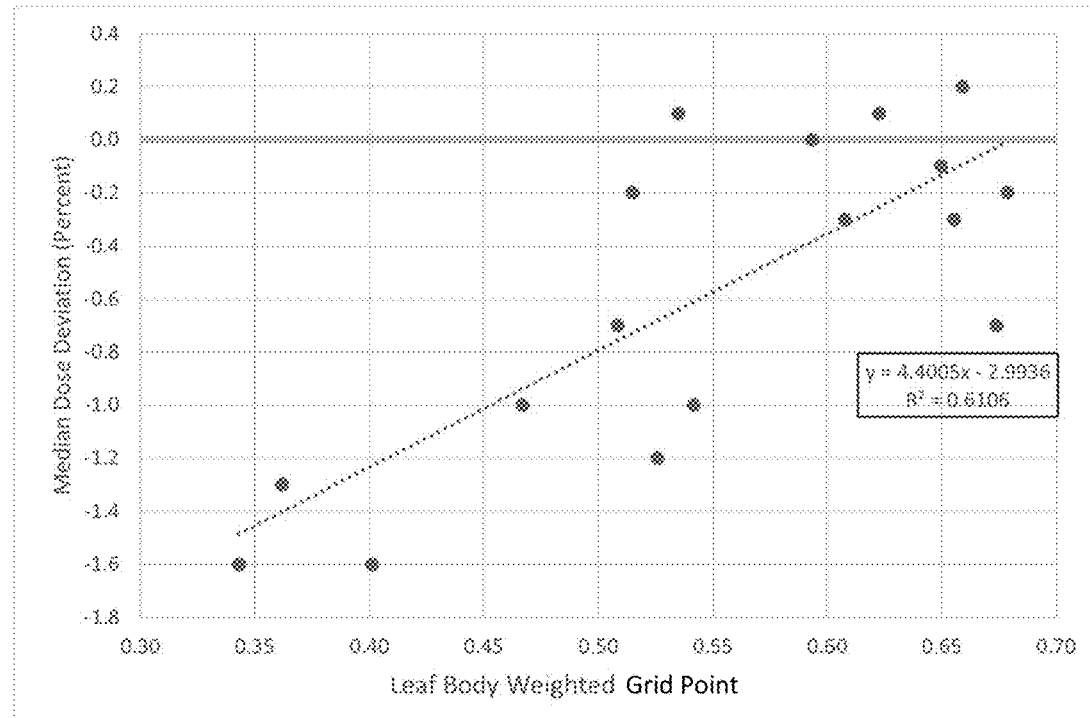
FIG. 6B is a graph of median dose deviation vs. plan MU-weighted average leaf body grid point fractions, in accordance with the present disclosure.
Figure 6C:
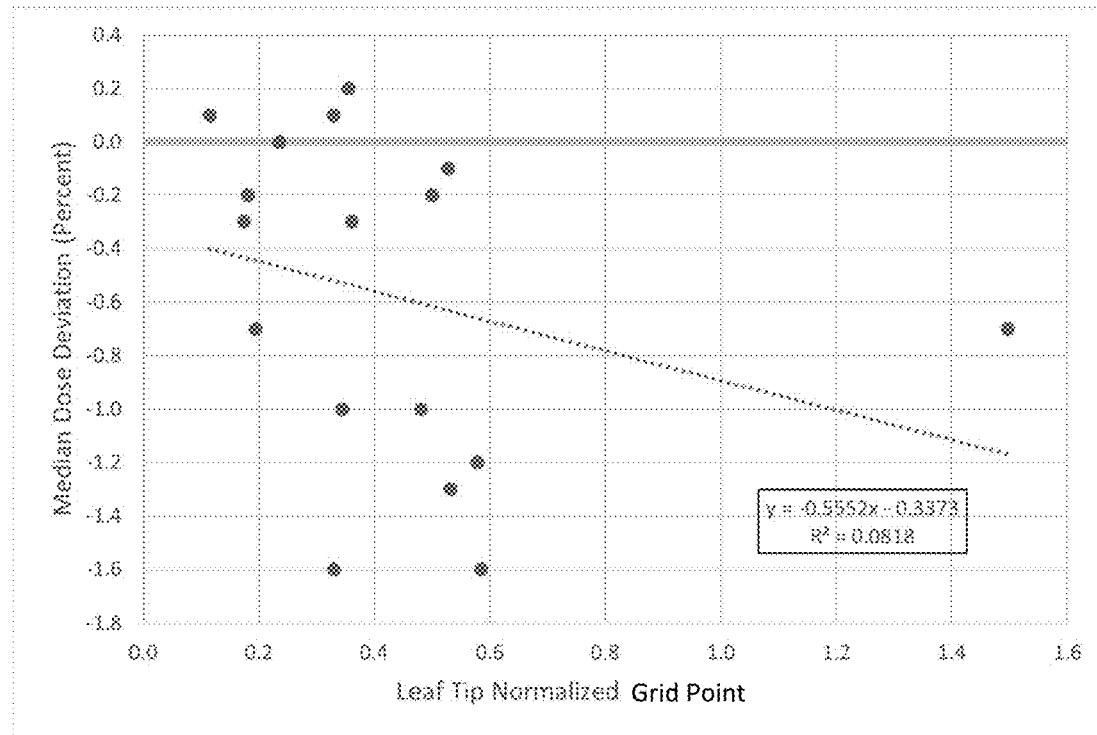
FIG. 6C is a graph of median dose deviation vs. plan MU-weighted average leaf tip grid point fractions normalized to the open field grid point fraction.
Figure 6D:
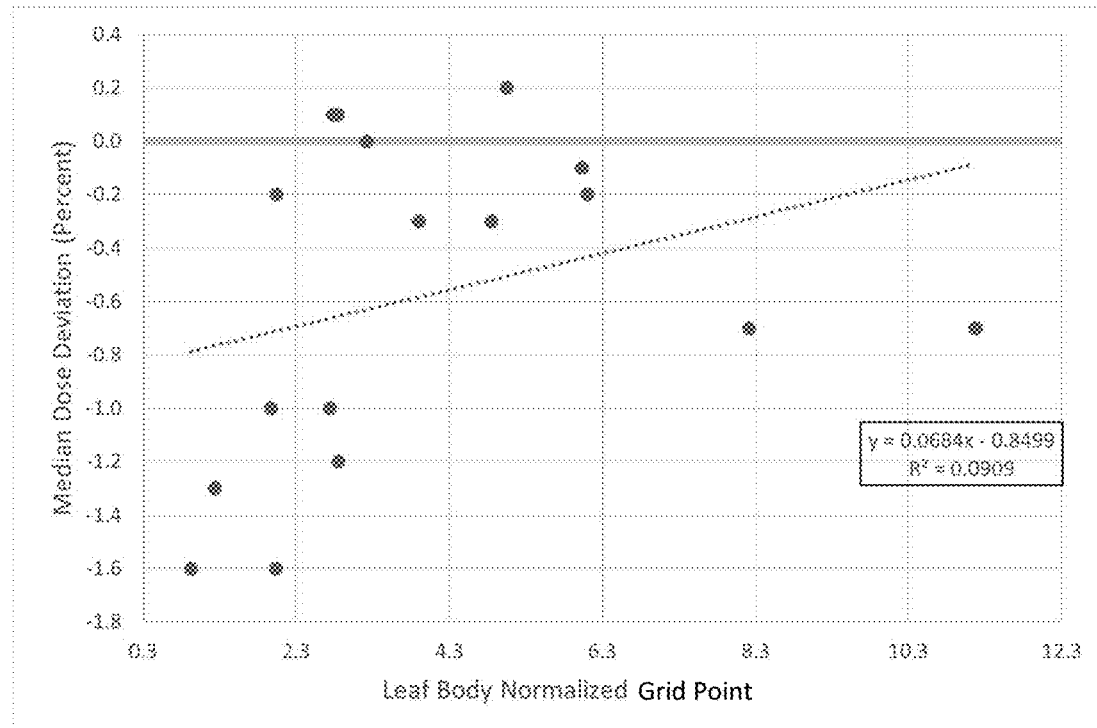
FIG. 6D is a graph of median dose deviation vs. plan MU-weighted average leaf body grid point fractions normalized to the open field grid point fraction.

The gamma analysis pass rate (2% local dose difference criterion, 2 mm distance-to-agreement criterion, 10% threshold) and median dose deviation of each plan were plotted with respect to the plan MU-weighted average grid point fractions, as illustrated in FIG. 5A (gamma analysis pass rates vs. plan MU-weighted average leaf tip grid point fractions) and FIG. 5B (gamma analysis pass rates vs. plan MU-weighted average leaf body grid point fractions). There is weak correlation between gamma pass rates and the two metrics In contrast, median dose deviation was found to correlate with the two average grid point fractions discussed previously. Plots of the relationships can be found in FIGS. 6A and 6B, and as normalized in FIGS. 6C and 6D. It is clear from FIGS. 6A and 6B that the correlation between average grid point fractions and median dose deviation is stronger than with gamma analysis pass rates. This correlation is not present after normalizing for the open field grid point fraction, as shown in FIGS. 6C and 6D.

The present invention has been described in terms of one or more preferred embodiments, and it should be appreciated that many equivalents, alternatives, variations, and modifications, aside from those expressly stated, are possible and within the scope of the invention.

The invention claimed is:

1. A system for assessing a radiation therapy plan, the system comprising:
   a radiation therapy system configured to deliver radiation therapy to subject based on a radiation therapy plan and including a multi-leaf collimator (MLC); and
   a computer system configured to:
      receive the radiation therapy plan;
      calculate at least one metric indicating transmission characteristics of a beam delivered according to the radiation therapy plan using a model of the MLC having a plurality of zones, wherein each zone is classified based on transmission characteristics;
      calculate a fraction of a total number of points or an area belonging to each zone;
      assess the at least one metric against a tolerance for variation between the radiation therapy plan and an implementation of the radiation therapy plan on the radiation therapy system; and
      generate an alert if the at least one metric is outside the tolerance.

2. The system of claim 1 wherein the at least one metric includes the fraction.

3. The system of claim 1 further comprising normalizing the fraction and the at least one metric includes the fraction after normalization.

4. A system for assessing a radiation therapy plan, the system comprising:
- a radiation therapy system configured to deliver radiation therapy to subject based on a radiation therapy plan and including a multi-leaf collimator (MLC); and
- a computer system configured to:
- receive the radiation therapy plan;
- calculate at least one metric indicating transmission characteristics of a beam delivered according to the radiation therapy plan using a model of the MLC having a plurality of zones, wherein each zone is classified based on transmission characteristics;
- assess the at least one metric against a tolerance for variation between the radiation therapy plan and an implementation of the radiation therapy plan on the radiation therapy system;
- generate an alert if the at least one metric is outside the tolerance; and
- wherein the computer system is further programmed to calculate a grid point fraction based on a fraction of a total number of points belonging to each zone to create a MU-weighted average that serves as the at least one metric.

5. The system of claim 4 wherein the MU-weighted average is given by:

$$\frac{\sum_{i=1}^{N} f_i * m_i}{\sum_{i=1}^{N} m_i};$$

where $f_i$ is a grid point fraction for an i-th control point, $m_i$ is a monitor units for the i-th control point, and N is a total number of control points in the radiation therapy plan.

6. The system of claim 5 wherein the MU-weighted average is a normalized MU-weighted average given by:

$$\frac{\sum_{i=1}^{N} \frac{f_i}{o_i} * m_i}{\sum_{i=1}^{N} m_i};$$

where $o_i$ is an open field grid point fraction at each control point.

7. The system of claim 1 wherein the computer system is further programmed to compare the at least one metric to a database of metrics about known radiation therapy plans to determine if the at least one metric is within the tolerance relative to similar known radiation therapy plans.

8. The system of claim 1 wherein the computer system is further programmed to receive an updated radiation therapy plan and repeat calculating, assessing, and generating using the updated radiation therapy plan.

9. A method for assessing a radiation therapy plan for implementation on a particular radiation therapy system including a multi-leaf collimator (MLC), the method comprising:
- receiving a radiation therapy plan;
- calculating at least one metric indicating transmission characteristics of a beam delivered using the particular radiation therapy system to perform the radiation therapy plan using a model of the MLC having a plurality of zones, wherein each zone is classified based on the transmission characteristics;
- calculating a fraction of a total number of points belonging to each zone;
- evaluating the at least one metric against a tolerance for variation between the radiation therapy plan and an implementation of the radiation therapy plan on the particular radiation therapy system; and
- generating an alert indicating that the at least one metric is outside the tolerance.

10. The method of claim 9 wherein the at least one metric includes the fraction.

11. The method of claim 9 further comprising normalizing the fraction and wherein the at least one metric includes the fraction after normalization.

12. A method for assessing a radiation therapy plan for implementation on a particular radiation therapy system including a multi-leaf collimator (MLC), the method comprising:
- receiving a radiation therapy plan;
- calculating at least one metric indicating transmission characteristics of a beam delivered using the particular radiation therapy system to perform the radiation therapy plan using a model of the MLC having a plurality of zones, wherein each zone is classified based on the transmission characteristics;
- calculating a grid point fraction based on a fraction of a total number of points belonging to each zone to create a MU-weighted average that serves as the at least one metric;
- evaluating the at least one metric against a tolerance for variation between the radiation therapy plan and an implementation of the radiation therapy plan on the particular radiation therapy system; and
- generating an alert indicating that the at least one metric is outside the tolerance.

13. The method of claim 12 wherein the MU-weighted average is given by:

$$\frac{\sum_{i=1}^{N} f_i * m_i}{\sum_{i=1}^{N} m_i};$$

where $f_i$ is a grid point fraction for an i-th control point, $m_i$ is a monitor units for the i-th control point, and N is a total number of control points in the radiation therapy plan.

14. The method of claim 13 wherein the MU-weighted average is a normalized MU-weighted average given by:

$$\frac{\sum_{i=1}^{N} \frac{f_i}{o_i} * m_i}{\sum_{i=1}^{N} m_i};$$

where $o_i$ is an open field grid point fraction at each control point.

15. The method of claim 9 further comprising comparing the at least one metric to a database of metrics about known radiation therapy plans to determine whether the at least one metric is within the tolerance relative to similar known radiation therapy plans.

16. The method of claim 9 further comprising receiving an updated radiation therapy plan and repeat calculating, assessing, and generating using the updated radiation therapy plan.

17. The method of claim 9 wherein the alert indicates that the radiation therapy plan should not be implemented on the radiation therapy system.

\* \* \* \* \*